(12) United States Patent
Ferguson

(10) Patent No.: US 6,364,741 B1
(45) Date of Patent: Apr. 2, 2002

(54) DISPOSABLE NURSING BRA

(76) Inventor: Bonnie S. Ferguson, 1338 Lisbon St., Morris, IL (US) 60450

( * ) Notice: Subject to any disclaimer, the term of this patent is extended or adjusted under 35 U.S.C. 154(b) by 0 days.

(21) Appl. No.: 09/933,150

(22) Filed: Aug. 21, 2001

Related U.S. Application Data

(60) Provisional application No. 60/296,143, filed on Jun. 7, 2001.

(51) Int. Cl.[7] .................................................. A41C 3/00
(52) U.S. Cl. .......................................... 450/57; 450/37
(58) Field of Search ........................ 450/36–38, 57–60, 450/54.55; 2/267, 268; 604/385.1, 388

(56) References Cited

U.S. PATENT DOCUMENTS

| | | | |
|---|---|---|---|
| 2,534,721 A | 12/1950 | Marshall | |
| 2,748,771 A | 6/1956 | Richards | |
| 3,507,285 A | 4/1970 | Williams | |
| 3,513,852 A | 5/1970 | Seidl | |
| 4,125,114 A | 11/1978 | Repke | |
| 4,674,510 A | 6/1987 | Sneider | |
| 5,149,336 A | * 9/1992 | Clarke et al. | 604/388 |
| 5,474,545 A | 12/1995 | Chikazawa | |
| 5,931,717 A | * 8/1999 | Lidjl | 450/37 |
| 6,074,273 A | 6/2000 | Turner et al. | |
| D433,786 S | * 11/2000 | Gladstone | D2/708 |

* cited by examiner

Primary Examiner—Gloria M. Hale
(74) Attorney, Agent, or Firm—Richard C. Litman

(57) ABSTRACT

A brassiere for lactating mothers which incorporates pelletized, absorbent material interposing cloth layers of the brassiere cup. Once the absorbent material is saturated with fluids, the entire brassiere may be disposed of and replaced with another.

9 Claims, 2 Drawing Sheets

DISPOSABLE NURSING BRA

CROSS-REFERENCE TO RELATED APPLICATION

This application claims the benefit of U.S. Provisional Patent Application Ser. No. 60/296,143, filed Jun. 7, 2001.

BACKGROUND OF THE INVENTION

1. Field of the Invention

The present invention generally relates to women's wearing apparel. More specifically, the present invention is drawn to a disposable nursing brassiere having a diaper-type absorbing layer to absorb and retain liquid, fluids or moisture which may leak or drain from the breast.

2. Description of Related Art

Recent medical studies have indicated that a baby's potential for improved health is enhanced when the baby is breast fed. Because of these findings, there has been a resurgence of mothers who breast feed their babies.

A continuing problem faced by lactating mothers is that of breast fluids (milk) which tend to leak and stain clothing, creating odor and causing discomfort and embarrassment. There are many brassieres in the marketplace which attempt to alleviate the aforementioned problem.

Examples of such brassieres are shown in U.S. Pat. No. 2,534,721 (Marshall), U.S. Pat. No. 2,748,771 (Richards), U.S. Pat. No. 3,513,852 (Seidl) and U.S. Pat. No. 6,074,273 (Turner et al.). All of the above cited brassieres are designed for repeated wear and employ a removable pad to absorb leakage from the breasts.

U.S. Pat. No. 4,125,114 (Repke) and U.S. Pat. No. 4,647,510 (Sneider) exemplify the structure of removable breast pads per se.

U.S. Pat. No. 5,474,545 (Chikazawa) discloses an absorbent article, such as a diaper, wherein the absorbent material is fabricated from biodegradable grains.

U.S. Pat. No. 3,507,285 (Williams) discloses a disposable brassiere made from inexpensive material. The brassiere of the instant patent includes no structure for specifically absorbing fluids which may leak from breasts.

None of the above inventions and patents, taken either singly or in combination, is seen to disclose a disposable brassiere having absorbent means as will subsequently be described and claimed in the instant invention.

SUMMARY OF THE INVENTION

The present invention is drawn to a brassiere to be used by nursing mothers. Unlike prior art nursing brassieres which mostly employ removable absorbent pads, the brassiere of the instant invention incorporates pelletized, absorbent material interposing cloth layers of the brassiere cup or surroundings. Once the absorbent material is saturated, the entire brassiere is to be disposed of and replaced with another.

The concept of disposing of the entire brassiere would greatly alleviate the problems now encountered with the removable pads in that there would be no residual leakage to the brassiere from the pad to cause odor and/or stain cloths. Also, time and energy are saved since the disposable brassiere requires no laundering.

As contemplated, the brassieres would be packaged in convenient quantities (six, twelve, twenty-four, etc.) for marketing purposes. A small number of brassieres could easily fit in a purse if the user plans to be out for an extended period. The brassiere would be fabricated in a range of sizes (small, medium, large, extra-large) to ensure universal appeal. Although designed especially for nursing mothers, it is obvious that the brassiere would find utility in scenarios that might require surgical procedures on the breasts (augmentation, implants, mastectomies, etc.). The brassiere will also serve medical purposes, such as nipple discharge, breast infection, abscesses, and swollen bumps or festering sores which may develop on the skin in advanced cancer.

Accordingly, it is a principal object of the invention to provide a brassiere to be employed by lactating mothers.

It is another object of the invention to provide a brassiere which incorporates a pelletized absorbent medium.

It is a further object of the invention to provide a brassiere which is fabricated from inexpensive and biodegradable materials.

Still another object of the invention is to provide a brassiere which is disposable.

It is an object of the invention to provide improved elements and arrangements thereof in a brassiere for the purposes described which are dependable and fully effective in accomplishing their intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
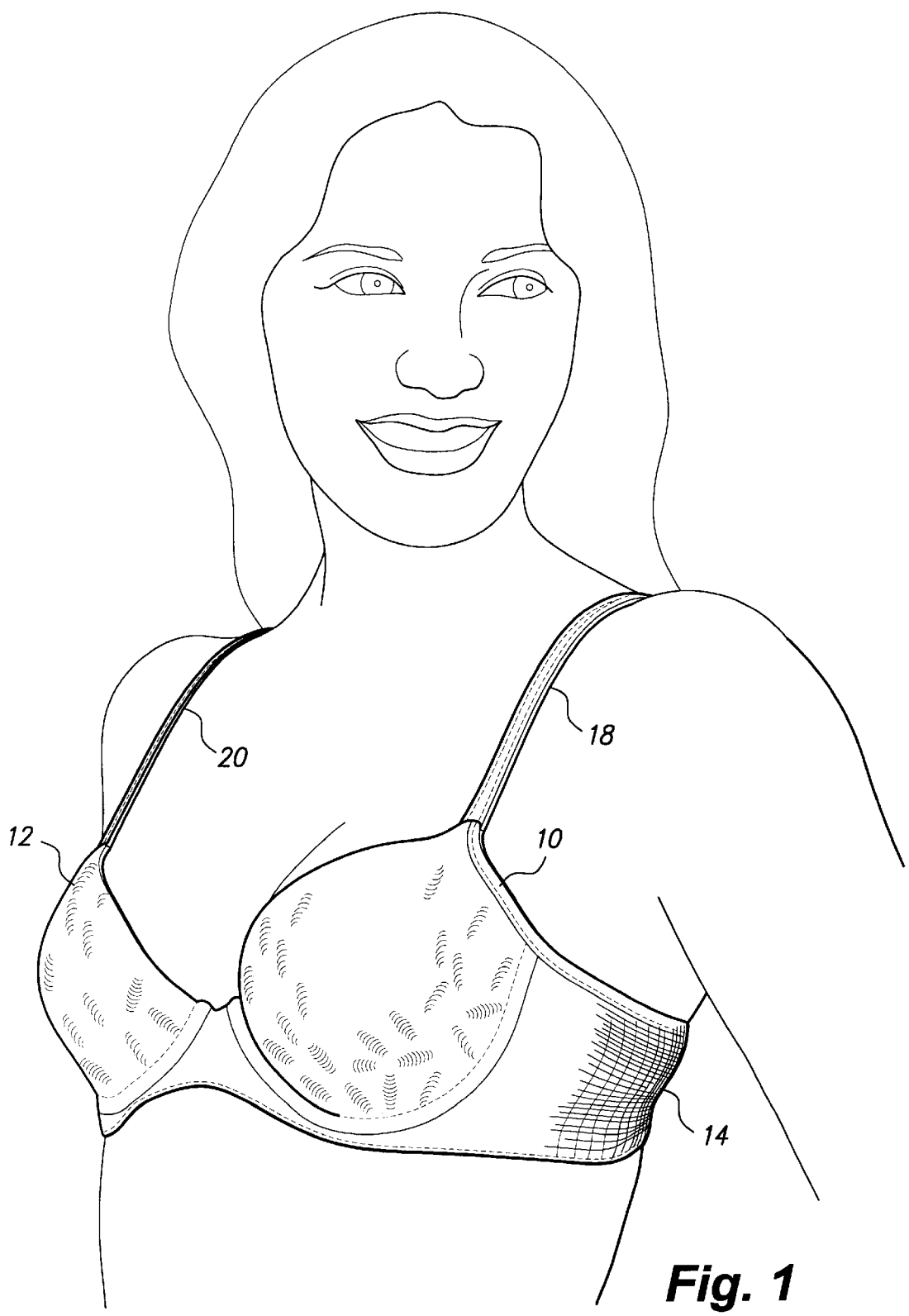
FIG. 1 is an environmental, perspective view of a disposable nursing brassiere according to the present invention.

As illustrated in FIG. 1 the brassiere of the present invention comprises identical cup members 10 and 12. Back bands 14 (only one is shown) extend rearwardly from the respective cup members and are adapted to be detachably secured together by fasteners in a conventional manner. A pair of support straps 18, 20 each have respective first ends secured to a top portion of a respective cup. The two second ends of each strap 18, 20 (not shown) are attached to a respective back band 14.

Figure 2:
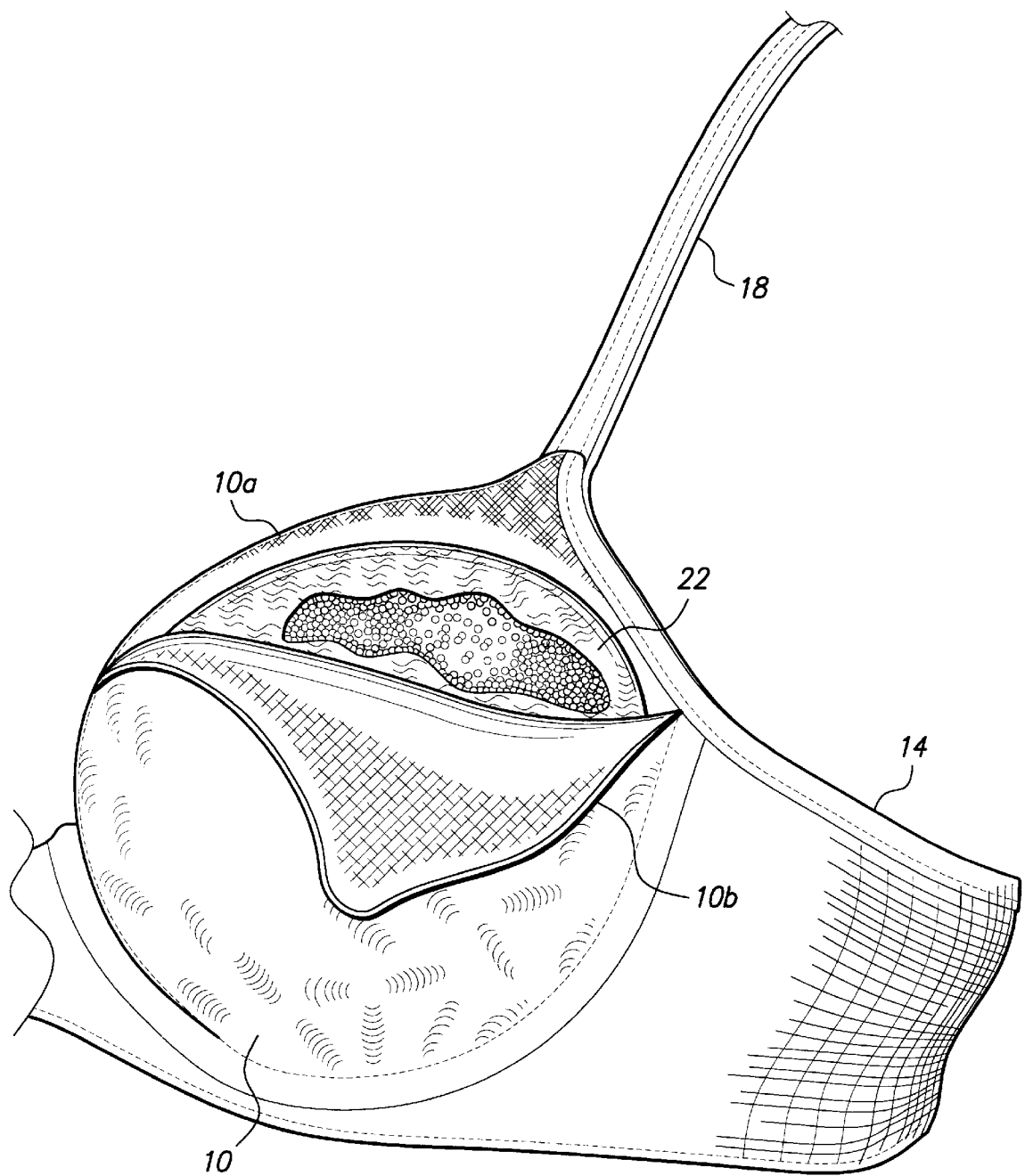
FIG. 2 is a partial, cutaway view of a disposable nursing brassiere according to the present invention.

Attention is now directed to FIG. 2 which illustrates the unique construction of the brassiere cup. Cup 10 comprises an inner layer of liquid permeable material 10a which is adapted to contact the breast. A liquid impermeable material 10b is disposed to form the outer layer of the cup or surroundings. Inner and outer layers 10a, 10b may be fabricated from any thin, suitable, inexpensive, biodegradable material (paper, compressed wood pulp, natural or synthetic fibers, etc.). Positioned between the inner and outer layers is a biodegradable, absorbent layer 22. Absorbent layer 22 comprises grains or pellets of highly absorbent material known in the art and commonly utilized in disposable diapers. Layer 22 is permanently encased between layers 10a and 10b by gluing or sewing the edges of the two layers together. Cup 12 is constructed in an identical manner.

As discussed above, when the absorbent layer becomes saturated, a user merely has to dispose of the soiled brassiere and don a fresh, new brassiere.

It is to be understood that the present invention is not limited to the sole embodiment described above, but encompasses any and all embodiments within the scope of the following claims.

I claim:

1. A disposable brassiere comprising:
   a right cup member having an inner layer and an outer layer;
   a left cup member having an inner layer and an outer layer, said left cup member attached to said right cup member;
   each said inner layer being fabricated from a liquid permeable material;
   each said outer layer being fabricated from a liquid impermeable material; and
   a pelletized material, said pelletized material disposed between said inner layer and said outer layer and incased therein.

2. A disposable brassiere as recited in claim 1, wherein said pelletized material is an absorbent material.

3. A disposable brassiere as recited in claim 2, including a pair of shoulder straps, wherein each said pair of shoulder straps is attached to a respective left cup member and right cup member.

4. A disposable brassiere as recited in claim 3, including at least one back band attached to said right cup member and said left cup member.

5. A disposable brassiere as recited in claim 4, wherein said inner layer, said outer layer, said pelletized material, said pair of shoulder straps and said at least one back band are fabricated from biodegradable material.

6. A disposable brassiere comprising:
   a right cup member having an inner layer and an outer layer;
   a left cup member having an inner layer and an outer layer, said left cup member attached to said right cup member;
   each said inner layer being fabricated from a liquid permeable, biodegradable material;
   each said outer layer being fabricated from a liquid impermeable, biodegradable material; and
   a biodegradable pelletized material, said biodegradable pelletized material disposed between each said inner layer and said outer layer and incased therein.

7. A disposable brassiere as recited in claim 6, wherein said pelletized material is an absorbent material.

8. A disposable brassiere as recited in claim 7, including a pair of shoulder straps, wherein each said pair of shoulder straps is attached to a respective left cup member and right cup member.

9. A disposable brassiere as recited in claim 8, including at least one back band attached to said right cup member and said left cup member.

* * * * *